United States Patent [19]

Fielding et al.

[11] Patent Number: 5,001,163

[45] Date of Patent: Mar. 19, 1991

[54] ORGANIC POLYMERIC MATERIAL AND ION-EXCHANGE MEMBRANE WITH PENDANT CARBOCYCLIC EXCHANGING GROUPS PRODUCED

[75] Inventors: Harold C. Fielding, Northwich; Philip H. Gamlen, Warrington; Ian M. Shirley, Weaverham, all of England

[73] Assignee: Imperial Chemical Industries PLC, London, England

[21] Appl. No.: 317,369

[22] Filed: Mar. 1, 1989

[30] Foreign Application Priority Data

Mar. 1, 1988 [GB] United Kingdom ............... 8804858

[51] Int. Cl.$^5$ .......................... C08J 5/20; C08F 14/18
[52] U.S. Cl. ........................................ 521/27; 521/38; 526/242; 526/243; 570/131; 570/132; 570/136; 570/138
[58] Field of Search ............... 570/131, 132, 136, 138; 521/38, 27; 526/242, 243

[56] References Cited

U.S. PATENT DOCUMENTS

| | | | |
|---|---|---|---|
| 3,083,238 | 3/1963 | Hauptschein et al. | 570/138 |
| 3,280,083 | 10/1966 | Butler | 570/131 |
| 4,321,339 | 3/1982 | Anderson et al. | 521/33 |

*Primary Examiner*—Peter F. Kulkosky
*Attorney, Agent, or Firm*—Cushman, Darby & Cushman

[57] ABSTRACT

An organic polymeric material, which is preferably perfluorinated and which comprises a polymeric chain and at least one group pendant from the chain, in which the group pendant from the chain comprises a saturated cyclic group and at least one ion-exchange group or group convertible thereto, and in which the ion-exchange group or group convertible thereto is linked to the polymeric chain through the cyclic group. Also an ion-exchange membrane produced from the polymeric material, an electrolytic cell containing the membrane, vinyl monomers from which the organic polymeric material may be produced and intermediates useful in production of the monomers.

26 Claims, No Drawings

ORGANIC POLYMERIC MATERIAL AND ION-EXCHANGE MEMBRANE WITH PENDANT CARBOCYCLIC EXCHANGING GROUPS PRODUCED

This invention relates to an organic polymeric material and to an ion-exchange membrane produced therefrom, particularly to an ion-exchange membrane which is useful in an electrolytic cell, especially in a chlor-alkali cell. The invention also provides novel monomeric materials from which the organic polymeric material may be produced and novel intermediates which are useful in the production of the monomeric materials.

Ion-exchange membranes made from organic polymeric materials having ion-exchange properties are used in a wide variety of applications, and the variety of applications of such membranes continues to increase. Such polymeric materials and membranes may contain fixed anionic groups and associated cations and be capable of exchanging cations, or they may contain fixed cationic groups and associated anions and thus be capable of exchanging anions, or the polymeric materials and the membranes may contain both fixed anionic groups and fixed cationic groups.

Ion-exchange membranes are useful in separation processes such as reverse osmosis and ultra filtration. For example, they find wide application in the desalination of sea-water and in the purification of brackish water and industrial effluent. Ion-exchange membranes are also finding wide applications in industry, for example, in the concentration of solutions of, for example, fruit juices and pharmaceuticals.

Ion-exchange membranes which are essentially hydraulically impermeable but which are permeable to cations or anions or both are finding increasing applications in electrochemical cells, for example in fuel cells, in electrolytic cells in which an electrolyte is electrolysed, and in electrolytic cells in which electrosynthesis is carried out. In recent years a major development has been in the use of cation-exchange membranes in chlor-alkali cells in which chlorine and aqueous alkali metal hydroxide are produced by the electrolysis of aqueous alkali metal chloride solution. In such a chlor-alkali cell a cation-exchange membrane is positioned between an anode and an adjacent cathode and during electrolysis cationic species are transported across the membrane between the anode compartments and cathode compartments of the cell. Where an aqueous alkali metal chloride solution is electrolysed in an electrolytic cell of this type the solution is fed to the anode compartments of the cell and chlorine produced in the electrolysis and depleted alkali metal chloride solution are removed from the anode compartments, hydrated alkali metal ions are transported across the membrane to the cathode compartments of the cell to which water or dilute alkali metal hydroxide solution is charged, and hydrogen and alkali metal hydroxide solution produced by the reaction of alkali metal ions with water are removed from the cathode compartments of the cell. In general the alkali metal chloride is sodium chloride, although it may be potassium chloride.

Although many organic polymeric materials have been proposed for use as membranes for such electrochemical cells in recent years perfluoroorganic polymers containing ion exchange groups, particularly fixed sulphonic and carboxylic groups, have found favour for use in chlor-alkali cells on account of the resistance of such perfluoroorganic polymers to chemical degradation in the cell.

An example of a perfluoroorganic polymer containing ion-exchange groups which has been proposed for use as an ion-exchange membrane is the perfluoroorganic polymer containing sulphonic groups described in GB patent 1034197. The perfluoroorganic polymer may, for example, contain units having the structures $$-CF_2-CF_2-$$

and $$-CF_2-CF_2- \text{ and } -CF_2-CF- \\ \qquad\qquad\qquad\qquad | \\ \qquad\qquad\qquad (OCF_2CFY)_nOCF_2CFR_fSO_2M$$

where $R_f$ is fluorine or a perfluoroalkyl group having from 1 to 10 carbon atoms, e.g. a perfluoromethyl group, n is 1, 2 or 3, Y is fluorine or a trifluoromethyl group, and M is fluorine, a hydroxyl group, an amino group, or a group having the formula —O Met, where Met is an alkali metal or a substituted or an unsubstituted ammonium group. The application of such a perfluoroorganic polymer as an ion-exchange membrane in a chlor-alkali cell is described in GB Patent 1402920.

Polymers of the type described are sold as membranes under the trade name 'Nafion' by E I DuPont de Nemours Inc. In a preferred perfluoroorganic polymer of the above structure Y is $CF_3$, n is 1 and $R_f$ if F.

A further example of a perfluoroorganic polymer containing ion-exchange groups which has also been proposed for use as an ion-exchange membrane is the perfluoroorganic polymer containing carboxylic groups described, for example, in GB Patents 1516048 and 1518387. Examples of such perfluoroorganic polymers include copolymers of tetrafluoroethylene and $$CF_2=CFOCF_2CF(CF_3)OCF_2CF_2CF_2COX,$$

$$CF_2=CFO(CF_2)_3OCF(CF_3)COX,$$

$$CF_2=CFO(CF_2)_4OCF(CF_3)COX, \text{ and}$$

$$CF_2=CFOCF_2CF(CF_3)OCF_2CF_2COX$$

where X is, for example, fluorine, a hydroxyl group, an oxyalkyl group, or a group having the formula OM, where M is an alkali metal or a quaternary ammonium group. Polymers of the type described are sold as membranes under the trade name 'Flemion' by Asahi Glass Co Ltd.

Many different types of perfluoroorganic polymers and combinations thereof for use as ion-exchange membranes in chlor-alkali cells have been proposed and those described above have been referred to merely by way of example. Thus, membranes made from polymers which contain both carboxylic and sulphonic groups have been proposed, as have membranes comprising laminates of two or more films of different polymers, for example, a laminate of a film of a perfluoroorganic polymer containing sulphonic groups and a film of a perfluoroorganic polymer containing carboxylic groups.

Most of the polymeric materials which have been proposed for use as ion-exchange membranes in chlor-alkali cells, and all of the polymeric materials which have been used commercially in such cells, are perfluoroorganic polymers, that is polymers containing ion-exchange groups in which the polymer is completely fluorinated such that the organic polymer is free of hydrogen atoms attached to carbon atoms. It has been found to be very desirable that the polymeric material be a perfluorinated polymer if it is to have acceptable stability and resistance to chemical degradation in the environment of a chlor-alkali cell, particularly in the presence of wet chlorine, chlorine-containing aqueous alkali metal halide solution, and aqueous alkali metal hydroxide solution. In general the perfluoroorganic polymers which have been proposed have been copolymers of tetrafluoroethylene and a perfluoro vinyl ether containing an ion-exchange group or groups.

The present invention relates to a novel organic polymeric material containing ion-exchange groups which is suitable for use in the form of an ion-exchange membrane, particularly an ion-exchange membrane in an electrolytic cell.

According to the present invention there is provided an organic polymeric material which comprises a polymeric chain and at least one group pendant from the chain, in which the group pendant from the chain comprises a saturated cyclic group and at least one ion-exchange group or group convertible thereto, and in which the ion-exchange group or the group convertible thereto is linked to the polymeric chain through the cyclic group.

The organic polymeric material of the invention is particularly suitable for use as an ion-exchange membrane, and in a further embodiment of the invention there is provided an ion-exchange membrane which comprises an organic polymeric material as described in the form of a substantially hydraulically impermeable sheet or film. The ion-exchange membrane is permeable to ions, which may be solvated, e.g. hydrated, but it is substantially hydraulically impermeable.

The ion-exchange membrane is particularly suitable for use as a membrane in an electrolytic cell, although it is not limited to such use, and in a further embodiment of the invention there is provided an electrolytic cell which comprises at least one anode and at least one cathode and an ion-exchange membrane as described positioned between an anode and adjacent cathode thereby dividing the cell into separate anode and cathode compartments.

The organic polymeric material of the invention may be produced by polymerising at least one vinyl monomer which comprises a saturated cyclic group and an ion-exchange group or group convertible thereto in which the ion-exchange group or group convertible thereto is linked to the vinyl group through the cyclic group, or by copolymerising at least one such vinyl monomer with an ethylenically unsaturated monomer which does not contain an ion-exchange group or group convertible thereto and/or with at least one vinyl monomer which contains an ion-exchange group or group convertible thereto which is not linked to the vinyl group through a cyclic group.

The copolymerisation may be effected in the presence of an ethylenically unsaturated monomer which does not contain an ion-exchange group or a group convertible thereto in order to introduce into the chain of the organic polymeric material units which do not contain an ion-exchange group or group convertible thereto and which may serve to modify the properties of the organic polymeric material and of the ion-exchange membrane produced therefrom, particularly the physical and/or the mechanical properties of the membrane, and the ion-exchange capacity thereof.

The organic polymeric material of the invention, particularly when in the form of an ion-exchange membrane, possesses a member of benefits and advantages. For example, it is possible to have more than one ion-exchange group or group convertible thereto forming a part of a pendant group, or of each pendant group, attached to the chain of the polymeric material, and thus it is possible to vary, and in particular to increase, the ion-exchange capacity of the organic polymeric material without the need to vary, and in particular to increase, the proportion of units in the organic polymeric material derived from the vinyl monomer containing the ion-exchange group or groups convertible thereto. Specifically, it is possible to achieve a relatively high ion-exchange capacity in an organic polymeric material which contains a relatively low proportion of units derived from the aforementioned vinyl monomer. Furthermore, in the organic polymeric material the ion-exchange groups or groups convertible thereto are linked to the polymeric chain through a cyclic group and it is possible, by suitable positioning of the ion-exchange groups or groups convertible thereto linked to the cyclic groups, and by suitable positioning of other substituent groups which are not ion-exchange groups linked to the cyclic groups, to vary the ion-exchanging activity of the former groups. For example, where the cyclic group is of the cyclohexyl structure and has a single ion-exchange group or group convertible thereto attached to the cyclic group the former group may be attached in a 2, 3 or 4 position in order that the activity of a given such group may be varied.

It is preferred that the organic polymeric material is a fluoropolymeric material as such materials are generally more resistant to attack by chemicals, e.g. acids and alkalis, with which the material may come into contact during use. Indeed, for many uses it is preferred that the organic polymeric material is a perfluoropolymeric material. Thus, an ion-exchange membrane made of a perfluoropolymeric material is preferred for use in a chlor-alkali cell in which chlorine and aqueous alkali metal hydroxide solution are produced by electrolysis of aqueous alkali metal chloride solution as such a membrane is particularly resistant to chemical attack by the electrolyte and by the products of electrolysis.

In the pendant group or groups of the organic polymeric material the cyclic group is saturated, that is it does not contain ethylenic unsaturation. Whilst we do not exclude the possibility of the organic polymeric material containing some groups pendant from the chain which comprise unsaturated groups, e.g. unsaturated cyclic groups, the presence of such unsaturated groups may be disadvantageous, particularly where the organic polymeric material is used in the form of an ion-exchange membrane in a chlor-alkali cell. Thus, when used as a membrane in a chlor-alkali cell such unsaturated groups may be subjected to chemical attack, e.g. chlorination of the unsaturated group and subsequent chemical attack by alkali. When in the form of a perfluorinated organic polymeric material the unsaturated group may also be susceptible to chemical attack by alkali. Thus, it is preferred that cyclic groups in the organic polymeric material consist essentially of saturated groups.

The organic polymeric material may comprise a fixed cationic group, that is a cationic group linked to the group pendant from the polymeric chain, and an associated anion, in which case the polymeric material will be an anion-exchange material. Alternatively, the organic polymeric material may comprise a fixed anionic group and an associated cation in which case the polymeric material will be a cation-exchange material. Materials of the latter type are generally of wider applicability, particularly when in the form of an ion-exchange membrane for use in an electrolytic cell. It is also possible that the organic polymeric material may comprise both fixed cationic and fixed anionic groups, and associated anions and cations respectively, such that the polymeric material will function both as an anion-exchange material and as a cation-exchange material.

Where the polymeric material is a cation exchange material suitable fixed anionic groups include groups of the sulphonic, carboxylic and phosphonic type.

For example, the group may have the structure —SO$_2$X, where X is OM and where M is H, or alkali metal, e.g. sodium or potassium, or an ammonium or quaternary ammonium group. Alternatively, X may be halogen, e.g. fluorine, in which case the group —SO$_2$X is not itself capable of ion-exchange. The latter group may be hydrolysed in order to convert it to a group which is itself capable of effecting ion-exchange. The group may have the structure —COY, where Y is OM and where M is H, or alkali metal, e.g. sodium or potassium, or an ammonium or quaternary ammonium group. Alternatively, Y may be halogen, e.g. fluorine, or oxyalkyl, in which case the group —COY is not itself capable of effecting ion-exchange. The latter group may be hydrolysed in order to convert it to a group which is itself capable of effecting ion-exchange.

Suitable anion-exchange groups, or groups convertible thereto include a group comprising quaternary ammonium, e.g. a group —N(alkyl)$_4$X where X is a halogen, e.g. —CH$_2$N(CH$_3$)$_3$ $^{+Cl-}$ or —CH$_2$NH—CH$_2$CH$_2$N(CH$_3$)$_3$$^{+Cl-}$.

For the sake of convenience the expression "ion-exchange group" will hereafter be used both for groups which are themselves capable of effecting ion-exchange and for groups which are not themselves capable of effecting ion-exchange but which may be converted, for example by hydrolysis, to groups which are capable of effecting ion-exchange.

The cyclic group in the groups pendant from the polymeric chain of the organic polymeric material may be a carbocyclic group or it may be a heterocyclic group, and it may comprise, for example, 4, 5 or 6 atoms. Suitable carbocylic groups include groups of the cyclohexyl or cyclopentyl type. Suitable heterocyclic groups may be oxygen- or nitrogen-containing, and examples include a saturated furan group and a saturated pyridyl group.

The ion-exchange group may be attached directly to the cyclic group in the groups pendant from the polymeric chain of the organic polymeric material, or indirectly to the cyclic group through a divalent group. Direct attachment of the ion-exchange group to the cyclic group provides greater scope for varying the activity of the ion-exchange group, for example by changing the position of the ion-exchange group on the cyclic group and/or by the attachment of other groups to the cyclic group the presence of which may result in some steric hinderence of the ion-exchange group and resultant change in the activity of the group. However, where the ion-exchange group is of the carboxylic type direct attachment of the ion-exchange group to the cyclic group may not be preferred, particularly where the organic polymeric material comes into contact with caustic alkali, such as when used in the form of an ion-exchange membrane in a chlor-alkali cell, as the caustic alkali may tend to decarboxylate the polymeric material. Indirect attachment of the carboxylic group to the cyclic group is preferred as polymeric materials containing such indirectly attached groups are less susceptible to decarboxylation.

The organic polymeric material may comprise ion-exchange groups of one type, or it may comprise ion-exchange groups of a plurality of different types. Indeed, the polymeric chain of the organic polymeric material may comprise pendant groups containing an ion-exchange group of one type and pendant groups containing an ion-exchange group of a different type, or the polymeric chain may comprise pendant groups at least some of which contain a plurality of ion-exchange groups which may be the same or different. It is the presence of a plurality of ion-exchange groups in the same pendant group which enables a relatively high ion-exchange capacity to be achieved in the organic polymeric material without the need to use a high proportion of units derived from the vinyl monomer containing the ion-exchange groups.

The cyclic group may be attached directly to he polymeric chain of the organic material or indirectly through a divalent group.

The organic polymeric material may comprise a polymeric chain of units having the structure

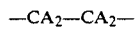

and units having the structure

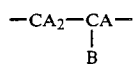

where A is hydrogen, halogen or alkyl and in which the groups A may be the same or different, and in which B is a group which comprises a saturated cyclic group and an ion-exchange group and in which the ion-exchange group is linked to the polymeric chain through the cyclic group. For reasons which have been disclosed previously it is preferred that at least some of the groups A are F, and it is more preferred that all of the groups A are F and that the group B is also fluorinated and more preferably perfluorinated.

Examples of the group B include the following

in which the cyclic group is saturated, in which D and E, which may be the same or different, are divalent groups or a direct link, in which the cyclic group may be hydrocarbyl or be partially or completely fluorinated, in which D and E, when divalent groups, may be partially or completely fluorinated, and in which n is an integer of at least 1. For example, n may be 1 or 2.

The group B may be a group having a similar structure but in which the group —DSO$_2$X is replaced by the group —(DCOY)$_n$, that is

Alternatively, the cyclic group may contain a group or groups —(DSO$_2$X)$_n$ and a group or groups —(DCOY)$_n$, that is the group B may have the structure

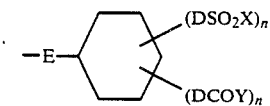

Examples of such groups B include the following

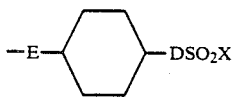

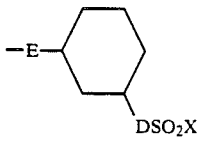

and

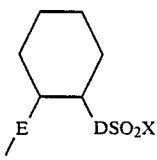

and

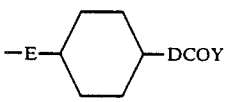

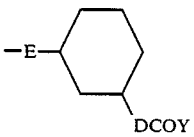

and

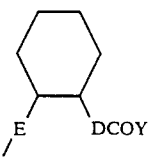

X and Y may be as hereinbefore referred to. Where D is a divalent group it may be, for example, —(CA$_2$)$_n$, where A is as hereinbefore described. In the case of an ion-exchange group of the carboxylic type it is preferred that the group D is a divalent group, for the reasons hereinbefore disclosed. The Group D may be for example, —CF$_2$—, as in

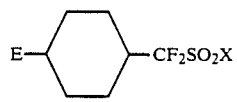

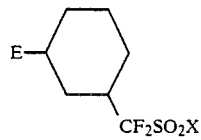

and

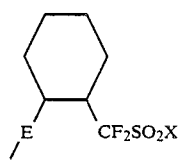

or as in

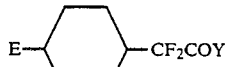

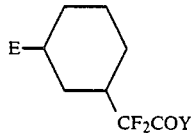

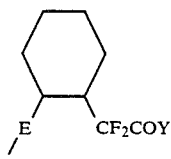

The group E through which the cyclic group is linked to the polymeric chain of the organic polymeric material, may be a direct link or a divalent group. It may be the same as or different from the group D, and it may comprise an ether group, for example a group —(OCF$_2$—CFRf)$_n$— where n is an integer, e.g. 1, 2 or 3, and Rf is F or a perfluoroalkyl group, or —(OCF$_2$—CFRf)$_n$O(CF$_2$)$_m$ where n and m are zero or an integer, e.g. 1, 2 or 3, and R$_f$ is F or a perfluoroalkyl group.

Other cyclic groups to which ion-exchange groups are attached, directly or indirectly, include, for example, groups having the structure

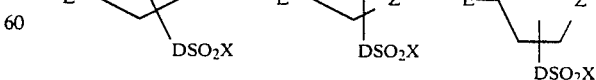

where Z is O or N and D and E are as hereinbefore described, and the cyclic group is partially or completely fluorinated, and groups in which —DSO$_2$X is replaced by —DCOY. Examples of such groups include

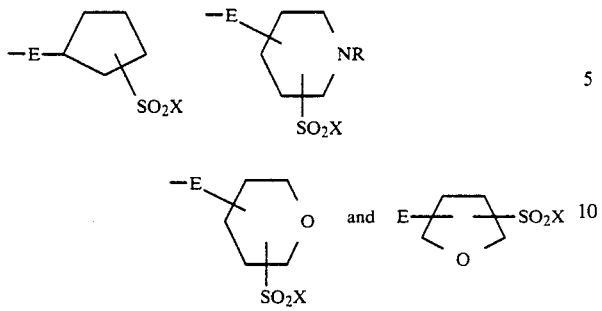

where R is an alkyl group, which may be perfluorinated.

The ion-exchange activity of the ion-exchange groups may be varied by having non-ion-exchange groups attached to the cyclic groups. Suitable such non-ion-exchange groups include, for example, alkyl groups, particularly perfluoroalkyl groups. The position of the non-ion-exchange group in relation to that of the ion-exchange group on the cyclic group has an effect on the ion-exchange activity of the ion-exchange group.

In the polymeric material the units which comprise a group pendant from the chain of the polymeric material which group comprises a cyclic group and an ion-exchange group linked thereto may be derived by polymerisation of a vinyl monomer which contains such a cyclic group and ion-exchange group. The vinyl monomer may have the structure $CA_2=CA-B$ where A and B have structures as hereinbefore described.

The organic polymeric material may be produced by copolymerisation of suitable monomers, for example, by compolymerisation of an olefine as hereinbefore described and having the structure

with a vinyl monomer as hereinbefore described having the structure

The organic polymeric material may be produced using known polymerisation techniques, for example, solution or dispersion polymerisation. Polymerisation may be effected under elevated pressure, indeed, the use of elevated pressure may be essential where a gaseous olefine is to be copolymerised, e.g. tetrafluoroethylene in which in the olefine $CA_2=CA_2$ A is F, and polymerisation may be initiated by known techniques, for example, by use of a free radical generator, e.g. a peroxide. The polymerisation may be effected at elevated temperature. The precise conditions under which the polymerisation is to be effected will depend at least in part on the precise nature of the monomers which are to be polymerised.

Merely by the way of example there are now disclosed vinyl ether monomers which contain a cyclic group and an ion-exchange group attached thereto and which may be polymerised to form units in the organic polymeric material of the invention. Such examples include

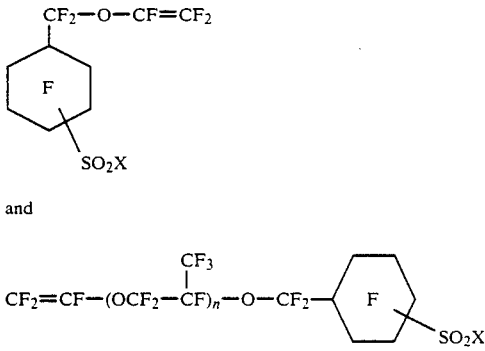

in which the —SO$_2$X group may be in the 2, 3 or 4 positions, in which the cyclic group is fully fluorinated and is saturated, and in which n is an integer of 1 to 3. (F within the cyclic group indicates that the group is perfluorinated).

In other specific examples of suitable vinyl ether monomers the —SO$_2$X group may be replaced by a group —CF$_2$COY.

Examples of vinyl ether monomers which contain a cyclic group and a plurality of ion-exchange groups attached thereto include

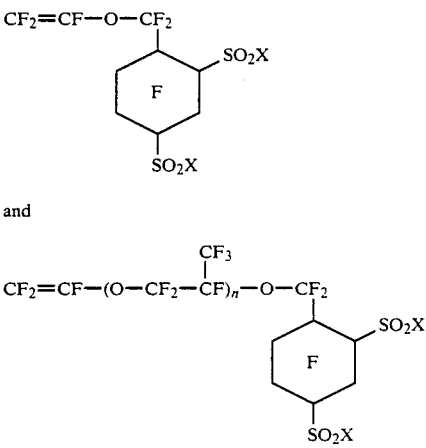

in which n is an integer of 1 to 3, and in which the cyclic group is fully fluorinated and is saturated, and the isomers in which the —SO$_2$X groups are in the 2,6 and 3,5 positions.

Other examples include

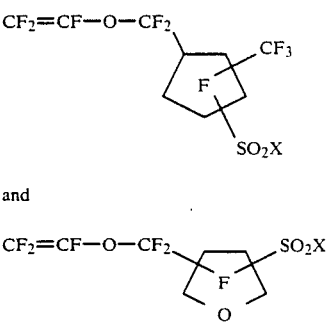

in which the cyclic group is fully fluorinated and is saturated.

The method of production of the vinyl monomer containing a cyclic group and having an ion-exchange group attached thereto will depend on the nature of the vinyl monomer which is to be produced. The production of several different vinyl monomers which may be polymerised to form the organic polymeric material of the invention will now be described by way of example. Certain of the vinyl monomers, and of the intermediates used in the production of the monomers, are novel and inventive materials in their own right and as such form part of the present invention. In each case production of the vinyl monomer from a known starting material will be described.

A. Production of a perfluorinated monomer of structure

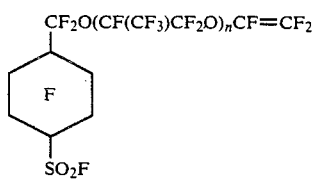

from pentafluorobenzoic acid, where n is zero or an integer.

1.

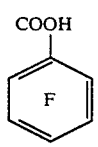

was reacted with a solution of NaSH in aqueous NaOH at a temperature of 70° C. to produce

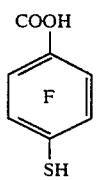

2. The thiol group in

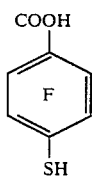

was then oxidised by reacting the latter with a solution of hydrogen peroxide in acetic acid solution to produce

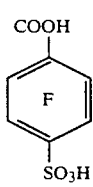

3.

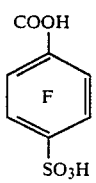

was then converted to the diacid fluoride by reacting the latter with $SF_4$ to produce

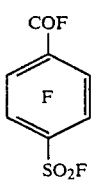

4.

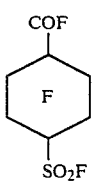

was then produced by fluorination of

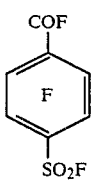

with a gaseous mixture of $F_2/N_2$ in a fluorocarbon solvent.

Alternatively,

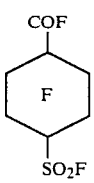

could have been produced by electrochemical fluorination of

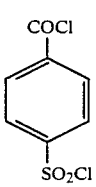

6.

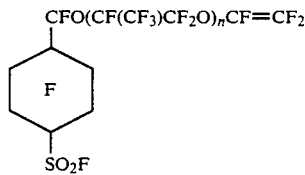

was then produced by pyrolysis of

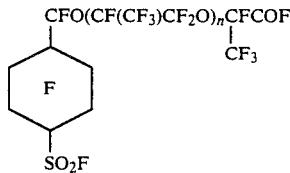

at a temperature of 240° to 400° C. in the vapour phase or at a temperature of 120° to 180° C. in the liquid phase.

B. Production of a perfluorinated monomer of structure

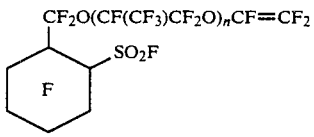

from perfluorobenzaldehyde, where n is zero or an integer.

1.

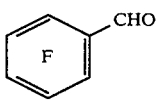

was reacted with rhodanine to produce

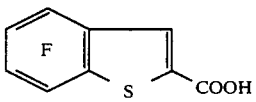

2. The product of step 1 above was then oxidised by reaction with a solution of potassium permanganate in water to produce

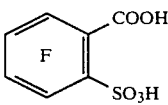

3. The product of step 2 was then fluorinated by reaction with $SF_4$ to produce the diacid fluoride

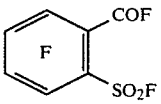

4.

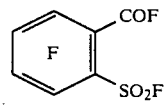

was then fluorinated with a gaseous mixture of $F_2/N_2$ in a fluorocarbon solvent to produce

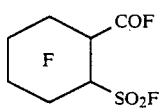

Alternatively

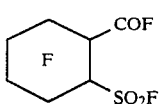

could have been produced by reacting

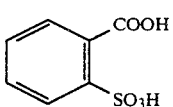

with $SF_4$ to produce

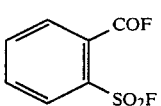

followed by electrochemical fluorination.

5.

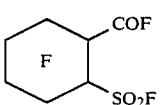

was then reacted with hexafluoropropylene oxide or chloropentafluoropropylene oxide to produce

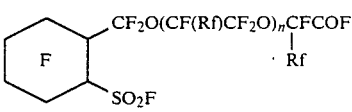

where Rf is $-CF_3$ or $-CH_2Cl$ and where n is zero or an integer, or a mixture in which n is zero and an integer. n is generally zero or from 1 to 3 depending on the proportion of the reactants.

6.

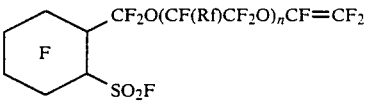

was then produced by pyrolysis of

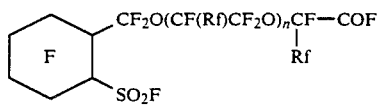

under conditions as hereinbefore described.

Certain of the vinyl monomers, and of the intermediates used in the production of the monomers form part of the present invention, and in one embodiment of the invention there is provided an intermediate having a structure which comprises a perfluorinated 6-membered carbocyclic ring having attached thereto two or more acidic groups, or derivatives thereof, in which at least two of the acidic groups have a different structure. The 6-membered ring may be saturated or unsaturated and it for example may have the structure

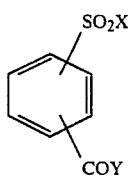

or it may be a saturated derivative thereof, in which X is OM where M is H or alkali metal, ammonium or quaternary ammonium, or halogen, and Y is OM where M is H or alkali metal ammonium or quaternary ammonium halogen or oxyalkyl. Specific examples of the structure include

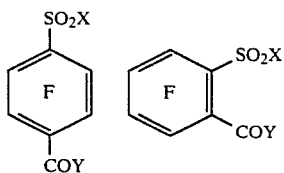

and saturated derivatives thereof, e.g.

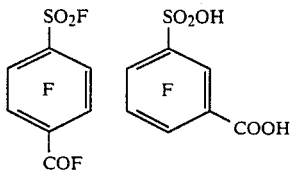

and saturated derivatives thereof.

Also forming a part of the present invention is a fully saturated intermediate having the structure

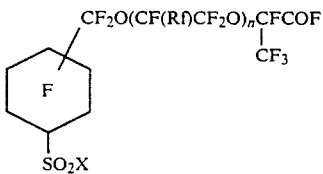

in which Rf is F or perfluoroalkyl and in which n is zero or an integer or in which n is an mixture of zero and an integer, and in which X is as hereinbefore described.

A vinyl monomer having the following structure also forms a part of the present invention

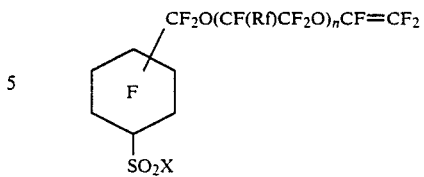

in which Rf is F or perfluoroalkyl and in which n is zero or an integer or in which n is a mixture of zero and an integer, and in which x is as hereinbefore described.

C. Production of a perfluorinated monomer of structure

where n is zero or an integer.

In the production of this monomer the reaction sequence which was followed is indicated as follows

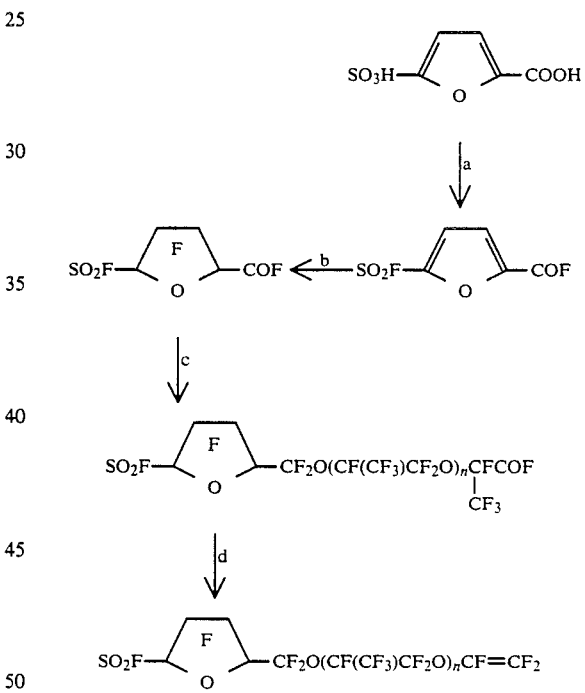

in which n is zero or an integer or a mixture of zero and an integer, and in which the reaction steps a to e are as follows a SF$_4$ at 80° C.

b F$_2$/N$_2$ in fluorocarbon solvent, or electrochemical fluorination c Hexafluoropropylene oxide/CsF in tetraglyme d Vapour phase pyrolysis The membrane of the invention is in the form of a thin sheet or film of the organic polymeric material. The sheet or film may be produced by a variety of different techniques which are known per se for use in the production of sheets or films of organic polymeric materials. For example, a membrane in the form of a sheet or film may be produced by melt extrusion of the polymeric material through a suitably shaped orifice, or by calendering of the polymeric material on a pair of rotating rolls, or by coating of a solution of the organic polymeric material upon a suitable substrate. The thickness of the membrane will depend at least to some extent on the manner in which the membrane is to be used. However, for many uses a thickness of the sheet or film in the range 50 to 500 microns will be suitable. The ion-exchange capacity, that is the concentration of ion-exchange groups in the organic polymeric material and in the ion-exchange membrane, may also vary over a wide range, and the ion-exchange capacity may well be determined by the manner in which the membrane is to be used. However, a suitable ion-exchange capacity for the organic polymeric material and for the membrane is in the range 0.4 to 4.0 milli equivalents of ion-exchange group per gramme of organic polymeric material or of ion-exchange membrane, although the ion-exchange capacity may be outside this range.

The ion-exchange membrane in the form of a thin sheet or film of the organic polymeric material may be laminated to a sheet or film of a similar or of a different organic polymeric material containing ion-exchange groups.

Although the ion-exchange membrane of the invention may be used in a wide variety of applications, for example in fuel cells and in the concentration of solutions, it is particularly useful as an ion-exchange membrane in an electrolytic cell, and the invention provides an electrolytic cell comprising at least one anode and at least one cathode and an ion-exchange membrane as described separating an adjacent anode and cathode thereby dividing the electrolytic cell into separate anode and cathode compartments. The electrolytic cell may be a monopolar cell containing a plurality of separate anodes and cathodes or it may be a bipolar cell containing a plurality of electrodes one side of which functions as an anode and the other side of which functions as a cathode. The electrolytic cell may be used to electrolyse a wide variety of different materials but it is particularly suitable for use in the electrolysis of aqueous alkali metal chloride solution, especially aqueous sodium chloride solution.

Where an aqueous alkali metal chloride solution is electrolysed in an electrolytic cell of the ion-exchange membrane type the solution is fed to the anode compartments of the cell and chlorine produced in the electrolysis and depleted alkali metal chloride solution are removed from the anode compartments, alkali metal ions are transported across the membranes to the cathode compartments of the cell to which water or dilute alkali metal hydroxide solution may be fed, and hydrogen and alkali metal hydroxide solution produced by the reaction of alkali metal ions with water are removed from the cathode compartments of the cell.

The electrodes in the electrolytic cell will generally be made of a metal or alloy and the nature of the metal or alloy will depend on whether the electrode is to be used as an anode or as a cathode and on the nature of the electrolyte which is to be electrolysed in the electrolytic cell.

Where aqueous alkali metal chloride solution is to be electrolysed and the electrode is to be used as an anode the electrode is suitably made of a film-forming metal or an alloy thereof, for example of zirconium, niobium, tungsten or tantalum but preferably of titanium, and the surface of the anode suitably carries a coating of an electro-conducting electrocatalytically active material. The coating may comprise one or more platinum group metals, that is platinum, rhodium, iridium, ruthenium, osmium or palladium, and/or an oxide of one or more of these metals. The coating of platinum group metal and/or oxide may be present in admixture with one or more non-noble metal oxides, particularly one or more film-forming metal oxides, e.g. titanium dioxide. Electro-conducting electrocatalytically active materials for use as anode coatings in an electrolytic cell for the electrolysis of aqueous alkali metal chloride solution, and methods of application of such coatings, are well known in the art.

Where aqueous alkali metal chloride solution is to be electrolysed and the electrode is to be used as a cathode the electrode is suitably made of iron or steel, or of other suitable metal, for example nickel. The cathode may be coated with a material designed to reduce the hydrogen overpotential of the electrolysis.

In the electrolytic cell the separate anode compartments of the cell will be provided with means for feeding electrolyte to the compartments, suitably from a common header, and with means for removing products of electrolysis form the compartments. Similarly, the separate cathode compartments of the cell will be provided with means for removing products of electrolysis from the compartments, and optionally with means for feeding water or other fluid to the compartments, suitably from a common header.

For example, where the cell is to be used in the electrolysis of aqueous alkali metal chloride solution the anode compartments of the cell will be provided with means for feeding the aqueous alkali metal chloride solution to the anode compartments and with means for removing chlorine and optionally with means for removing depleted aqueous alkali metal chloride solution from the anode compartments, and the cathode compartments of the cell will be provided with means for removing hydrogen and cell liquor containing alkali metal hydroxide from the cathode compartments, and optionally, and if necessary, with means for feeding water or dilute alkali metal hydroxide solution to the cathode compartments.

The invention is illustrated by the following Examples.

EXAMPLE 1

Production of 4-sulphotetrafluorobenzoic acid

424 g of pentafluorobenzoic acid (2.0 moles) were added, with stirring, to 160 g of sodium hydroxide (4.0 moles) dissolved in 2 liters of water to give a clear solution. 200 g NaSH (70% flake equivalent to 140 g NaSH (2.5 moles)) were added to the solution and the resultant mixture was heated to 70° C., with stirring. After stirring for 2 hours at 70° C. the resultant clear yellow solution was cooled in ice and neutralised with concentrated HCl (approximately 750 ml). The resultant white slurry was extracted with ether (4×500 ml). the extract was dried over MgSO$_4$, and the ether was removed on a rotary evaporator. The resultant white powder was dried at 80° C. under vacuum to give 407 g of 4-mercapto tetrafluorobenzoic acid product.

in a yield of approximately 90%.

The structure of the product was confirmed by infra red, NMR, and mass spectrographic analysis. The above process steps were repeated to build up a stock of 4-mercapto tetrafluorobenzoic acid for use in a further step of the process.

440 g of 4-mercapto tetrafluorobenzoic acid were dissolved in 1700 ml of glacial acetic acid. The resultant solution was stirred and heated to 80° C. on a water bath and 800 ml of 30% w/v aqueous solution of hydrogen peroxide was added dropwise over 2 hours. The resultant solution was cooled to 20° C. and 68 g of sodium metabisulphite were added to the solution to destroy any excess hydrogen peroxide.

The resultant solution was evaporated on a rotary evaporator at 80° C. under vacuum to give a pale orange coloured solid. The solid was dissolved in 260 ml of water and 60 ml of concentrated HCl were added. The resultant solution was extracted with ethyl acetate (1×600 ml and 3×250 ml) and the isolated product was then re-extracted into water by shaking the combined ethyl acetate extracts with 1×500 ml and 3×250 ml portions of water.

The water was removed on a rotary evaporator to give an off-white powder, which was dried at 80° C. and 0.7 m bar pressure to give 322 g of 4-sulpho tetrafluorobenzoic acid product in a yield of 66%.

The structure of the product was confirmed by infra red, NMR and mass spectrographic analysis.

EXAMPLE 2

Production of 4-fluorosulphonyl perfluorocyclohexane carbonyl fluoride

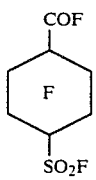

100 g of 4-sulpho tetrafluorobenzoic acid prepared as described in Example 1 were dried in a 500 ml Hasteloy autoclave with 100 ml of thionyl chloride at 80° C. for 1 hour. The excess thionyl chloride, and SO$_2$ and HCl produced by reaction of the thionyl chloride with water, were removed under vacuum. The autoclave was then cooled in liquid nitrogen and 78 g of SF$_4$ were distilled into the autoclave. The autoclave was then warmed to 20° C. and stirring was commenced. The autoclave was then heated to 80° C. for 18 hours, cooled and vented. The product, a brown liquid, solidified on standing. The product was dissolved in CF$_2$ClCFCl$_2$, treated with dry NaF to remove traces of HF, and the solution was filtered. Gas chromotographic and mass spectrographic analysis showed the solution to contain 4-fluorosulphonyl tetrafluorobenzoyl fluoride and 4-fluorosulphonyl heptafluorotoluene in yields of approximately 70% and 10% respectively the structures of which were confirmed by infra red and NMR analysis.

40 g of 4-fluorosulphonyl tetrafluorobenzoyl fluoride which had been separated from the above solution by distillation and 850 ml of CF$_2$ClCFCl$_2$ were charged to a glass reactor equipped with a condenser, a high speed stirrer, and a cooling bath. The contents of the reactor were cooled to −35° C. and stirred, and a 50/50 v/v mixture of F$_2$/N$_2$ was passed through the reactor at a rate of 50 ml/min. The temperature of the solution in the reactor was maintained at −35° C. and after 30 hours gas chromatographic analysis showed no trace of 4-fluorosulphonyl tetrafluorobenzoyl fluoride in the solution and that the solution contained 4-fluorosulphonyl perfluorocyclohexane carbonyl fluoride

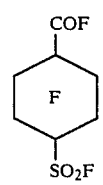

and perfluorocyclohexane carbonyl fluoride

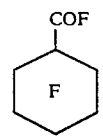

The 4-fluorosulphonyl perfluorocyclohexane carbonyl fluoride was separated from the solution by distillation and its structure confirmed by infra red and NMR analysis.

EXAMPLE 3

Production of 4-fluorosulphonyl perfluorocyclohexane carbonyl fluoride

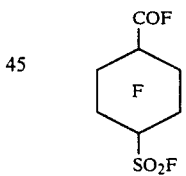

by electrochemical fluorination of 4-chlorosulphonyl benzoyl chloride

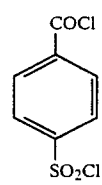

A one liter Simons cell was charged with 800 g of anhydrous hydrogen fluoride and the cell was run at 5.0 volts for 19 hours in order to dry the electrolyte. To the dry electrolyte there was added 48 g of 4-chlorosulphonyl benzoyl chloride in one charge and the electrolysis was continued at 6.0 volts at a cell temperature of 20° C. After 24 hours operation, a lower layer of liquid fluorocarbon products (18 g) was drained from the cell and treated with dry sodium fluoride to remove excess hydrogen fluoride.

4-fluorosulphonyl perfluorocyclohexane carbonyl fluoride was separated from the liquid fluorocarbon mixture by distillation and its structure was confirmed by mass spectrographic and NMR analysis.

EXAMPLE 4

Production of

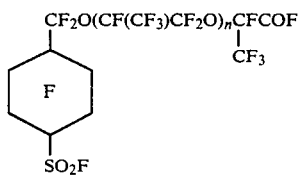

17.6 g of 4-fluorosulphonyl perfluorocyclohexane carbonyl fluoride produced as described in Example 2 was added to 20 ml of dry tetraglyme containing 0.24 g of dry caesium fluoride in a 125 ml autoclave. The resultant mixture was stirred for half an hour under an atmosphere of dry nitrogen, then cooled to $-60°$ C., the autoclave was evacuated, and 20 g of hexafluoropropylene oxide was distilled into the autoclave. The mixture was then allowed to warm to room temperature and was stirred overnight. The lower fluorocarbon layer (20 g) was recovered and was shown by gas chromatographic and mass spectrographic analysis to consist mainly of a mixture of products of the above formula in which n is 0 and n is 1 in a ratio of approximately 5:1. The structure of the product was confirmed by mass spectrographic and infra red analysis.

EXAMPLE 5

Production of

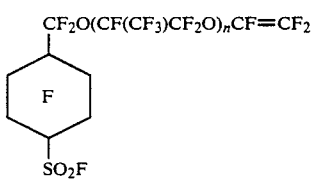

Nitrogen carrier gas, preheated to 200° C., was passed through a vaporisation flask heated in an oil bath at 220° C. 20 gm of the product from Example 4 were injected dropwise via a syringe pump into the vaporisation flask at the rate of 0.8 ml/min. The resulting gas stream was fed into the base of a fluidised bed 15 cm high and containing 100 cm$^3$ of 60 mesh glass beads at a temperature of 340° C. The flow rate was chosen to give a contact time of approximately 10 seconds and the fluorocarbon products (11.2 g) were condensed from the effluent gas stream in a series of cold traps. The main product was shown by mass spectrographic and infra red analysis to be

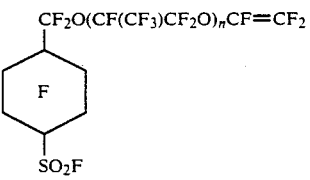

in which n=0 with some product in which in the above structure n=1. The product comprised a small proportion of an adduct of the above structure with HF.

EXAMPLE 6

Production of organic polymeric material containing ion-exchange groups or groups convertible thereto.

15 g of a distilled fraction of the product produced in Example 5 which was shown by gas chromatographic analysis to contain 98% of

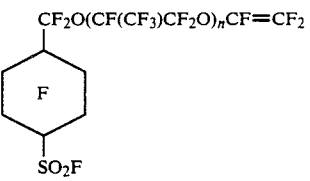

was charged to a 0.5 liter jacketed autoclave equipped with a gas inlet, stirrer and thermocouple, and 200 ml of deionised water, 0.2 g ammonium persulphate and 0.3 g ammonium perfluorooctanoate were also charged to the autoclave. The autoclave was then alternatively evacuated and swept with nitrogen to remove air and the mixture in the autoclave was emulsified by stirring at room temperature for 2 hours in an atmosphere of nitrogen. The autoclave was again evacuated and charged with tetrafluoroethylene to 10 bar pressure and then slowly heated to 80° C., with stirring. The autoclave was repressurised with tetrafluoroethylene each time the pressure dropped to 6 bar until the accummulated pressure drop indicated that 15 g of tetrafluoroethylene had been charged to the autoclave. The autoclave was cooled, vented and the emulsion removed. A small amount (4.5 g) of perfluorovinyl ether separated as a lower layer and the remaining emulsion was frozen in order to recover the copolymer which had been produced. The copolymer was filtered, washed with deionised water and dried under vacuum at 80° C. to give 16.2 gms of white copolymer. A sample of the copolymer was hot pressed to give a clear, tough film showing a peak in the infra red at 1460 cm$^{-1}$ (—SO$_2$F).

A 200 micron thick hot pressed film of the copolymer was hydrolysed in 25% NaOH in aqueous ethanol (75% H$_2$O, 25% ethanol) at 75° C. for 12 hours to give a film shown by titration to have an ion-exchange capacity of 0.9 milliequivalents/g.

EXAMPLE 7

Production of organic polymeric material containing ion-exchange groups or groups convertible thereto (alternative process).

10 g of a distilled fraction of the product produced in Example 5 which was shown by gas chromatographic analysis to contain 98% of

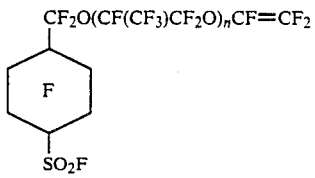

were dissolved in 200 ml of $CF_2ClCFCl_2$ containing 0.1 g azobisisobutyronitrile and the solution was charged to a 400 ml jacketed autoclave equipped with gas inlet, stirrer and thermocouple. The autoclave was swept with nitrogen, evacuated, and tetrafluoroethylene was charged to the autoclave to a pressure of 10 bar. The autoclave was heated to 75° C. and the contents were stirred and further tetrafluoroethylene was charged each time the pressure dropped to 8 bar, until the accummulated pressure drop indicated that 10 gm of tetrafluoroethylene had been charged. The autoclave was then cooled and the resultant copolymer dispersion recovered.

The copolymer was recovered by filtration, washed with $CF_2ClCFCl_2$ and dried under vacuum at 80° C. to give 5.6 g of white powder. Infra red examination of a hot pressed film produced from the powder showed absorption at 1460 cm$^{-1}$ ($-SO_2F$).

EXAMPLE 8

Production of 2-sulpho tetrafluorobenzoic acid

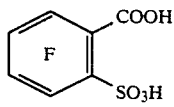

and 2-fluorosulphonyl tetrafluorobenzoyl fluoride

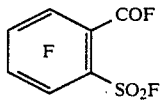

38 g of triethylamine were added dropwise to a well stirred suspension of 50 g of rhodanine and 70 g of pentafluorobenzaldehyde in 100 ml of chloroform, the temperature being held below 40° C. by external cooling. After one hour, the solution was washed with dilute HCl, then water. The solvent was removed and the resultant yellow residue recrystallised from IMS/water to give 82 g of 2,3,4,5,6-pentafluorobenzylidene rhodanine having a melting point of 132–135° C.

78 g of 2,3,4,5,6-pentafluorobenzylidene rhodanine were added in small portions to a stirred solution of 68 g of NaOH in 300 ml of water. The resultant clear red solution was heated to 90° C. for one hour, cooled in ice, acidified with concentrated HCl, and the cream coloured solid which was produced was filtered and washed. The crude product (59 g) was purified by sublimation to give 4,5,6,7-tetrafluorobenzothiophen-2-carboxylic acid having a melting point of 200° C.

A solution of 158 g of $KMnO_4$ in 1.5 liters of warm water was added to a stirred slurry of 49.7 g of 4,5,6,7-tetrafluorobenzothiophen-2-carboxylic acid and 27.6 g of $K_2CO_3$ in 200 ml water at such a rate as to maintain the temperature around 50° C. When addition was complete the mixture was heated to 100° C. for 3 hours, then cooled and filtered to remove $MnO_2$. The filter cake was washed with hot water and the combined aqueous layers were acidified with concentrated HCl.

The aqueous phase was concentrated on a rotary evaporator at 80° C. under vacuum to give a wet slurry. This slurry was extracted several times with ethyl acetate, the combined organic layers were dried over $MgSO_4$, filtered and the solvent was removed to give 23.5 g of a product, shown by $^{19}F$, $^{13}C$, $^1H$ nuclear magnetic resonance and mass spectrographic analysis to be 2-sulphotetrafluorobenzoic acid

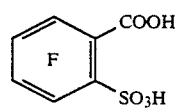

14.6 g of 2-sulphotetrafluorobenzoic acid was refluxed with 64 g of thionyl choride for 5 hours, cooled to room temperature, and diluted with 100 ml of methylene chloride. Filtration and removal of volatiles under vacuum gave 6.6 g of an orange gum, shown by $^{19}F$ $^{13}C$ nuclear magnetic resonance analysis and by infra red analysis to be the anhydride

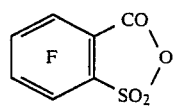

8.0 g of the crude anhydride was transferred under nitrogen to a warm dry 50 ml autoclave as a solution in 20 mls dry methylene chloride. The methylene chloride was removed by warming the autoclave under vacuum. The autoclave was then cooled in liquid nitrogen and 7 g of $SF_4$ transferred into the autoclave under vacuum. The sealed autoclave was then heated to 140° C. for 12 hours, cooled and vented. 7.5 g of brown liquid was recovered which solidified on the addition of hexane. Gas chromatographic/mass spectrographic analysis showed the product to be mainly 2-fluorosulphonyl tetrafluorobenzoyl fluoride,

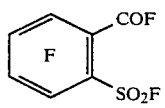

together with a small amount of 2-fluorosulphonyl heptafluorotoluene. Infra red examination of the main product showed peaks at 1890 cm$^{-1}$ ($-COF$) and 1460 cm$^{-1}$ ($-SO_2F$).

EXAMPLE 9

Production of

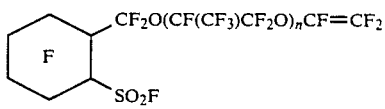

The procedures of Examples 2, 4 and 5 above were followed except that in place of the 4-fluorosulphonyl tetrafluorobenzoyl fluoride there was used 2-fluorosulphonyl tetrafluorobenzoyl fluoride produced as described in Example 8.

EXAMPLE 10

Use of ion-exchange membrane in electrolytic cell.

The 200 micron thick hydrolysed film produced as described in Example 6 was installed in an electrolytic cell equipped with a titanium mesh anode coated with $RuO_2/TiO_2$, and a nickel cathode, each comprising a series of parallel vertical blades, the film being positioned between the anode and cathode and in contact therewith. An electrolyte of a saturated aqueous solution of sodium chloride was charged continuously to the anode compartment of the cell and water was charged continuously to the cathode compartment of the cell. Chlorine and depleted solution were removed continuously from the anode compartment and hydrogen and a 20% by weight aqueous solution of sodium hydroxide were removed continuously from the cathode compartment. The cell temperature was maintained at 88° C. and electrolysis was conducted at a constant current density of 3 $KAm^{-2}$ and a cell voltage of 3.5 V.

We claim:

1. An organic fluoropolymeric material which comprises a polymeric chain and at least one group pendant from the chain, in which the group pendant from the chain comprises a saturated 4, 5 or 6 membered carbocyclic group and at least one cation-exchange group or group convertible thereto, and in which the cation-exchange group or group convertible thereto comprises fixed anionic groups of sulphonic, carboxylic or phosphonic type and is linked to the polymeric chain through the cyclic group.

2. An organic polymeric material as claimed in claim 1 in which the fluoropolymeric material is a perfluoropolymeric material.

3. An organic polymeric material of claim 2 in which the cyclic groups in the groups pendant from the chain consist essentially of saturated groups.

4. An organic polymeric material of claim 3 in which the organic polymeric material comprises fixed anionic groups and associated cations.

5. An organic polymeric material as claimed in claim 1 in which the sulphonic group has the structure —$SO_2X$, where X is OM and where M is H, or alkali metal, ammonium or quaternary ammonium, or halogen.

6. An organic polymeric material as claimed in claim 5 in which X is F.

7. An organic polymeric material as claimed in claim 1 in which the carboxylic group has the structure —COY, where Y is OM and where M is H, or alkali metal, ammonium or quaternary ammonium, halogen, or oxyalkyl.

8. An organic polymeric material as claimed in claim 7 in which Y is oxyalkyl.

9. An organic fluoropolymeric material as claimed in claim 1 which comprises a polymeric chain of units having the structure

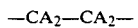

and units having the structure

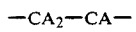

in which A is hydrogen, halogen, or alkyl and comprises at least some F, in which B is a group which comprises a saturated 4, 5 or 6 membered carbocyclic group and a cation-exchange group or group convertible thereto, and in which the cation-exchange group or group convertible thereto comprises fixed anionic groups of the sulphonic, carboxylic or phosphoric type and is linked to the polymeric chain through the cyclic group.

10. An organic polymeric material as claimed in claim 9 in which the group B has the structure

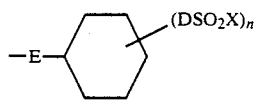

in which D and E are a direct link or a divalent group, n is an integer of at least 1, and X is OM where M is H, or alkali metal, ammonium or quaternary ammonium, or halogen.

11. An organic polymeric material as claimed in claim 9 in which the group B has the structure

in which D and E are a direct link or a divalent group, n is an integer of at least 1, and Y is OM where M is H or alkali metal, ammonium or quaternary ammonium, halogen, nitrile or oxyalkyl.

12. An organic polymeric material of claim 11 in which the cyclic group is a perfluorinated group.

13. An organic polymeric material of claim 12 in which the group B has the structure

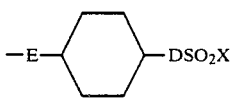

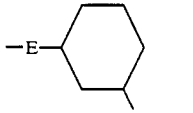

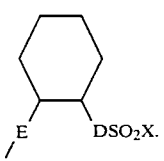

14. An organic polymeric material as claimed in claim 13 in which D has the structure —$CF_2$—.

15. An organic polymeric material of claim 12 in which the group B has the structure

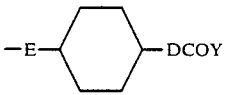

-continued

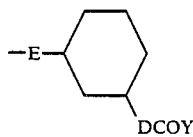

or

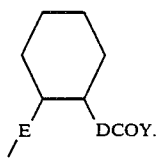

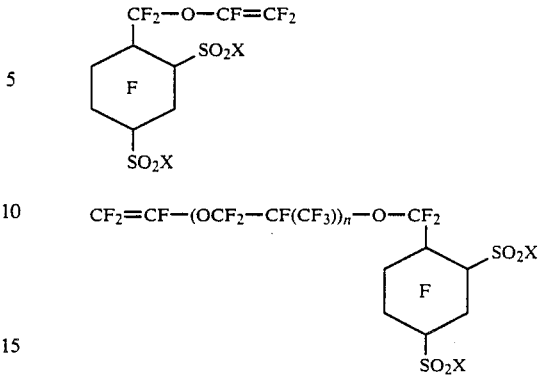

in which n is zero or an integer of 1 to 3, and in which the cyclic group is fully fluorinated and is saturated.

16. An organic polymeric material as claimed in claim 15 in which D has the structure —$CF_2$—.

17. An organic polymeric material of claim 16 in which E has the structure —$(OCF_2—CFRf)_n$—where n is an integer and Rf is F or a perfluoroalkyl group, or the structure —$(OCF_2CFRf)_nO(CF_2)m$ where n and m are zero or an integer, and Rf is F or a perfluoroalkyl group.

18. An organic polymeric material of claim 9 in which A is F.

19. An organic polymeric material of claim 1 which comprises units derived by polymerisation of a monomer having the structure

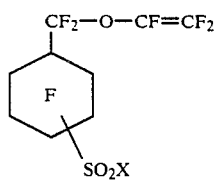

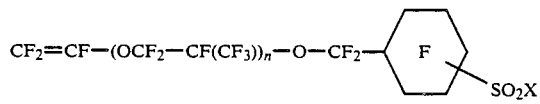

in which the —$SO_2X$ group may be in the 2, 3 or 4 positions, in which the cyclic group is fully fluorinated and is saturated, and in which n is a zero or an integer of 1 to 3.

20. An organic polymeric material of claim 19 which comprises units derived by polymerisation of a monomer having the structure 21. An organic polymeric material of claim 20 in which the organic polymeric material is produced by copolymerisation of the monomer with tetrafluoroethylene.

22. An organic polymeric material of claim 1 which contains 0.4 to 4.0 milliequivalents of cation exchange groups per gram of organic polymeric material.

23. An cation exchange membrane which comprises an organic polymeric material of claim 1 in the form of a substantially hydraulically impermeable sheet or film.

24. An cation exchange membrane as claimed in claim 23 in which the sheet or film has a thickness in the range 50 to 500 microns.

25. An cation exchange membrane as claimed in claim 24 in which contains 0.4 to 4.0 milliequivalents of cation exchange groups per gram of membrane.

26. A polymerisable vinyl monomer having the structure

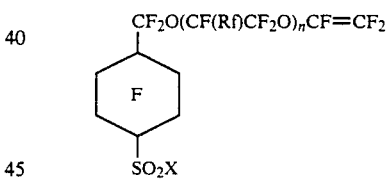

in which Rf is F or perfluoroalkyl and in which n is zero or an integer or in which n is a mixture of zero and an integer and in which X is OM where M is H, or alkali metal, ammonium or quaternary ammonium, or halogen.

* * * * *